US007060500B2

(12) United States Patent
Metz et al.

(10) Patent No.: US 7,060,500 B2
(45) Date of Patent: Jun. 13, 2006

(54) SINGLE-STRANDED OLIGODEOXYNUCLEOTIDE MUTATIONAL VECTORS

(76) Inventors: Richard A. Metz, 37 Winthrop Rd., Lawrenceville, NJ (US) 08648; Bruce L. Frank, 16 Meer Dr., Langhorne, PA (US) 19053; Debra M. Walther, 725 Timber La., Langhorne, PA (US) 19047

( * ) Notice: Subject to any disclaimer, the term of this patent is extended or adjusted under 35 U.S.C. 154(b) by 540 days.

(21) Appl. No.: 10/292,856

(22) Filed: Nov. 12, 2002

(65) Prior Publication Data

US 2004/0023392 A1    Feb. 5, 2004

Related U.S. Application Data

(60) Division of application No. 09/645,889, filed on Aug. 25, 2000, now Pat. No. 6,479,292, which is a continuation-in-part of application No. 09/384,960, filed on Aug. 27, 1999, now Pat. No. 6,271,360.

(51) Int. Cl.
*C12N 15/63* (2006.01)
*C12N 15/88* (2006.01)
*C12N 15/87* (2006.01)
*A01N 43/04* (2006.01)
*C07H 21/02* (2006.01)

(52) U.S. Cl. ...................... 435/458; 435/455; 435/458; 435/463; 435/490; 514/44; 536/23.1; 536/26.6

(58) Field of Classification Search ..................... None
See application file for complete search history.

(56) References Cited

U.S. PATENT DOCUMENTS

| | | | |
|---|---|---|---|
| 5,565,350 A | 10/1996 | Kmiec | |
| 5,731,181 A | 3/1998 | Kmiec | |
| 5,750,669 A | 5/1998 | Rosch et al. | |
| 5,756,325 A | 5/1998 | Kmiec | |
| 5,760,012 A | 6/1998 | Kmiec | |
| 5,780,296 A | 7/1998 | Holloman et al. | |
| 5,795,972 A | 8/1998 | Kmiec | |
| 5,808,044 A | 9/1998 | Brush et al. | |
| 5,871,984 A | 2/1999 | Kmiec | |
| 5,888,983 A | 3/1999 | Kmiec et al. | |
| 5,908,777 A | 6/1999 | Lee et al. | |
| 5,945,339 A | 8/1999 | Holloman et al. | |
| 6,004,804 A | 12/1999 | Kumar et al. | |
| 6,271,360 B1 | 8/2001 | Metz et al. | |

FOREIGN PATENT DOCUMENTS

| | | |
|---|---|---|
| WO | WO 93/04701 | 3/1993 |
| WO | WO 96/40271 A | 12/1996 |
| WO | WO 98/49350 | 11/1998 |
| WO | WO 99/07865 | 2/1999 |
| WO | WO 99/40789 | 8/1999 |
| WO | WO 99/58723 | 11/1999 |

OTHER PUBLICATIONS

Bandyopadhyay et al., 1999, "Nucleotide Exchange in Genomic in Genomic DNA of Rat Hepatocytes Using RNA/DNA Oligonucleotides", J. of Biol. Chem. 274: 10163-10172.

Beetham et al., 1999, "A tool for functional plant genomics: Chimeric RNA/DNA oligonucleotides cause in vivo gene-specific mutations", Proc. Natl. Acad. Sci. USA 96 : 8774-8778.

Boussif et al., 1995, "A versatile vector for gene and oligonucleotide transfer into cells in culture and invivo: Polyethylenimine", Prc Natl Acad Sci USA 92: 7297-7301.

Campbell et al., 1989, "Homologous Recombination Involving Small Stranded Oligonucleotides in Human Cells", 1: 223-227.

Chan et al., 1999, "Targeted Corrected of an Episomal Gene in mammalian cells by a short DNA fragment tethered to a triplex-forming oligonucleotide", J. of Biolog. Chem. 274: 11541-11548.

Eckart-Schuppe and Klaus, 1999, "Radiation inducible DNA repair processes in eukaryotes", Biochimie 81: 161-171.

Goncz et al., 1998, "Targeted replacement of a normal and mutant CFTR sequences in human airway epithelial cells using DNA", Human Molecular Genetics 7: 1913-1919.

Hunger-Bertling et al., 1990, "Short DNA Fragments induce site specific recombination in mammalian cells", Molec and Cellular Biochem 92: 107-116.

Kren et al., 1998, "In vivo site directed mutagenesis of the factor IX gene by chimeric RNA/DNA oligonucleotides", Nature Medicine 285-91.

Kunzelmann et al., 1996, "Gene targeting of CFTR DNA in CF epithelial cells", Gene Therapy 3: 859-867.

Moerschell et al., 1988, "Transformation of yeast with synthetic oligonucleotides", Proc Natl Acad Sci USA 85: 524-28.

Nicklin et al., "Pharmokinetic Properties of Phosphorothioates in Animals—Absorption, Distribution, Metablolism, and Elimination", Chapter 4, Handbook of Experimental Pharmacology, vol. 131.

Zhu et al., 1999, "Targeted manipulation of maize genes in vivo using chimeric RNA/DNA oligonucleotides", Proc Natl Acad Sci US/96: 8768-8773.

Gilar et al., 1998, "Study of phosphorothiate-modified oligonucleotide resistance to 3'-exonuclease using capillary electrophoresis", Journal of Chromatography, 714(1)::13-20.

Majumdar et al., 1998, "Targeted gene knockout mediated by triple helix forming oligonucleotides", Nature Genetics, 20(2):212-214.

Wang et al., 1996, "Mutagenesis in Mammalian Cells Induced by Triple Helix Formation and Transcription-Coupled Repair", Science 271:802-805.

*Primary Examiner*—David Guzo
*Assistant Examiner*—Laura McGillem
(74) *Attorney, Agent, or Firm*—Jones Day

(57) ABSTRACT

The invention concerns the introduction of predetermined genetic changes in target genes of a living cell by introducing an oligodeoxynucleotide encoding the predetermined change. The oligodeoxynucleotides are effective in animal, plant and bacterial cells. Specific end modifications that greatly increase the effectiveness of the oligodeoxynucleotides in bacteria are described. Surprisingly, unmodified oligodeoxynucleotides can be as effective in mammalian cells, including in vivo hepatocytes, as the modified nucleotides and can be as effective or more effective than chimeric oligonucleotides that consist of a mixture of deoxynucleotides and 2'-O-methyl ribonucleotides.

22 Claims, No Drawings

SINGLE-STRANDED OLIGODEOXYNUCLEOTIDE MUTATIONAL VECTORS

The present application is a divisional application of U.S. application Ser. No. 09/645,889, filed Aug. 25, 2000, now U.S. Pat. No. 6,479,292, which is a continuation-in-part application of U.S. application Ser. No. 09/384,960, filed Aug. 27, 1999, now U.S. Pat. No. 6,271,360, the disclosure of each of which is incorporated herein by reference in its entirety.

1. FIELD OF THE INVENTION

The invention concerns single-stranded oligodeoxynucleotides, certain derivatives thereof and methods of their use for introducing a predetermined change at a predetermined location in a target gene in a living cell. The cell can be a mammalian, insect, worm or avian cell, either in an artificial culture medium or in an organism, a bacterial cell or a plant cell. The target gene can be a chromosomal gene or an extrachromosomal gene, i.e., on a bacterial artificial chromosome.

2. BACKGROUND OF THE INVENTION

Techniques of making a predetermined change at a predetermined location in a target nucleic acid sequence of a cell have been described. These techniques utilize the cell's enzymes that concern DNA repair and homologous recombination. In these techniques an oligonucleotide or oligonucleotide analog is synthesized that contains two regions that have the sequence of the target gene that flank a region, termed a "mutator region", that differs from the target gene. In this application such oligonucleotides and analogs will be generically termed "mutational vectors". Such mutational vectors can introduce predetermined genetic changes into a target gene by a mechanism that is believed to involve homologous recombination and/or nucleotide excision and repair.

U.S. Pat. No. 5,565,350 and No. 5,731,181 to Kmiec describe mutational vectors that contain complementary strands wherein a first strand comprises ribonucleotide analogs that form Watson-Crick base pairs with deoxyribonucleotides of a second strand. U.S. Pat. No. 6,004,804 to Kumar and Metz describes certain improvements in duplex mutational vectors, including a variant in which the mutator region is present on only one of the two strands. The use of Kmiec type mutational vectors in mammalian systems is described in U.S. Pat. No. 5,760,012 and in conjunction with macromolecular carriers in International Patent Publication WO 98/49350 to Kren et al., and in related U.S. patent application Ser. No. 09/108,006. Additional descriptions of the use of Kmiec type mutational vectors can be found in Cole-Strauss et al., 1996, Science 273:1386; Kren et al., 1998, Nature Med. 4:285; and Bandyopadhyay et al., 1999, J. Biol. Chem. 274:10163.

The use of Kmiec type mutation vectors in plant cells is described in International Patent Publications WO 99/25853 to Pioneer Hi-Bred International, WO 99/07865 to Kimeragen, Inc. and WO 98/54330 to Zeneca Ltd. Scientific publications that describe the use of Kmiec type vectors in plants include Beetham et al., 1999, Proc. Natl. Acad. Sci. USA 96:8774 and Zhu, et al.,1999, Proc. Natl. Acad. Sci. USA 96:8768.

The use of Kmiec type mutational vectors and variants thereof, which are double stranded, is described in U.S. Pat. No. 6,004,804 to Kumar and Metz. The application of Kumar and Metz teaches, inter alia, that Kmiec type vectors and variants thereof can be used in bacterial cells.

The use of single stranded oligodeoxynucleotides as mutational vectors to effect changes in a chromosomal gene in the yeast, *S. cerevisiae*, was described in reports from laboratory of Dr. F. Sherman, Yale University. Moerschell et al., 1988, Proc. Natl. Acad. Sci. USA, 85:524–528 and Yamamoto et al., 1992, Yeast 8:935–948. The optimum length of the mutational vectors used in these studies was 50 nucleotides.

An isolated report of the use of a 160 nucleotide single and double stranded polynucleotide to attempt to make alterations in a chromosomal gene can be found at Hunger-Bertling, 1990, Mol. Cell. Biochem. 92:107–116. The results for single stranded polynucleotides were ambiguous because only the product of the experiments using double-stranded polynucleotides were analyzed.

The use of single stranded DNA fragment of 488 base pairs to make specific genetic changes in the cystic fibrosis transmembrane conductance regulator gene has been reported by Goncz et al., 1998, Hum. Mol. Genetics 7:1913; and Kunzelmann et al., 1996, Gene Ther. 3:859.

Single stranded oligodeoxynucleotides of about 40 nucleotides in length in mammalian cells were used as a control for studies of episomal genes in which the oligodeoxynucleotide was covalently linked to a triplex forming oligonucleotide and that the oligodeoxynucleotide alone resulted in rates of predetermined genetic change of the episomal gene of about 1 per $5 \times 10^{4}$, or fewer. Chan et al., 1999, J. Biol. Chem. 74:11541. An earlier report of the use of single-stranded oligodeoxynucleotide to make predetermined changes in an episomal gene in a mammalian cell is found in Campbell et al., 1989, The New Biologist 1:223.

One aspect of the invention concerns oligodeoxynucleotides that have been modified by the attachment of an indocarbocyanine dye. Indocarbocyanine dyes are known as excellent fluorophores. The synthesis of blocked indocarbocyanine β cyanoethyl N,N-diisopropyl phosphoroamidites that are suitable for use in solid phase nucleotide synthesis is described in U.S. Pat. Nos. 5,556,959 and No. 5,808,044.

A second aspect of the invention concerns a composition comprising a single stranded oligonucleotide encoding a predetermined genetic change and a macromolecular carrier that comprises a ligand for a receptor on the surface of the target cell. A composition comprising a poly-L-lysine, a ligand for the asialoglycoprotein receptor and an antisense oligodeoxynucleotide of between 21 and 24 nucleotides is described in International Patent Publication WO 93/04701.

A third aspect of the invention concerns a modification of a oligodeoxynucleotide by the attachment of a 3'-3' linked nucleotide. U.S. Pat. No. 5,750,669 teaches such a modified oligodeoxynucleotide.

Citation or identification of any reference in Section 2, or any section of this application shall not be construed as an admission that such reference is available as prior art to the present invention.

3. SUMMARY OF THE INVENTION

The present invention is based on the unexpected discovery that single-stranded oligodeoxynucleotides, particularly when appropriately modified or placed in a composition with a suitable macromolecular carrier, can be as or more effective in making predetermined genetic changes to target genes in cells as the prior art, i.e., Kmiec type mutational vectors. A single stranded oligodeoxynucleotide suitable for use according to the present invention is termed hereafter a Single-Stranded Oligodeoxynucleotide Mutational Vector or a SSOMV.

In one embodiment the invention provides for a composition for use in making changes to the chromosomal genes of animal, e.g. mammalian, cells consisting of the oligodeoxynucleotide encoding the genetic change and a macromolecular carrier. The carrier can be either a polycation, an aqueous-cored lipid vesicle or a lipid nanosphere. In a further embodiment that is suitable for in vivo use, the carrier further comprises a ligand that binds to a cell-surface receptor that is internalized such as a lignad for a clathrin-coated pit receptor, e.g., the asialoglycoprotein receptor, the folic acid receptor or the transferin receptor. In preferred embodiments the oligodeoxynucleotide is modified by the attachment of 3' and 5' blocking substituents such as a 3'-3' linked cytosine nucleotide and a 5' linked indocarbocyanine dye. In an alternative embodiment the modification can consist of the replacement of the 3' most and/or 5' most internucleotide phosphodiester linkage with a non-hydrolyzeable linkage such as a phosphorothioatediester linkage or a phosphoramidate linkage.

In a second embodiment the invention provides for the modification of the 3' and 5' end nucleotides of the oligodeoxynucleotide that encodes the predetermined genetic change. The invention is further based on the unexpected discovery that certain such modifications do not block the effectiveness of the oligodeoxynucleotide to produce genetic changes. One such embodiment is the combination of a 3'-3' linked cytosine nucleotide and a 5' linked indocarbocyanine dye. So modified, the oligodeoxynucleotides are more than 50 fold more effective than a corresponding unmodified oligodeoxynucleotides when used to make genetic changes in bacterial cells.

In a third embodiment the invention provides compounds and methods for the introduction of a predetermined genetic change in a plant cell by introducing an oligodeoxynucleotide encoding the predetermined genetic change into the nucleus of a plant cell.

In preferred embodiments the oligodeoxynucleotide is modified by the attachment of 3' and 5' blocking substituents such as a 3'-3' linked cytosine nucleotide and a 5' linked indocarbocyanine dye. In an alternative embodiment the modification can consist of the replacement of the 3' most and 5' most internucleotide phosphodiester linkage with a non-hydrolyzeable linkage such as a phosphorothioatediester linkage or a phosphoramidiate linkage. Alternatively, a 5' linked indocarbocyanine dye and 3' most internucleotide phosphodiester linkage a non-hydrolyzeable linkage can be used in yet a third embodiment.

The present invention may be understood more fully by reference to the following detailed description and illustrative examples of specific embodiments.

4. DETAILED DESCRIPTION OF THE INVENTION

The sequence of the SSOMV is based on the same principles as prior art mutational vectors. The sequence of the SSOMV contains two regions that are homologous with the target sequence separated by a region that contains the desired genetic alteration, termed the "mutator region". The mutator region can have a sequence that is the same length as the sequence that separates the homologous regions in the target sequence, but having a different sequence. Such a mutator region causes a substitution. Alternatively, the homologous regions in the SSOMV can be contiguous to each other, while the regions in the target gene having the same sequence are separated by one, two or more nucleotides. Such a SSOMV causes a deletion from the target gene of the nucleotides that are absent from the SSOMV. Also, the sequence of the target gene that is identical to the homologous regions may be adjacent in the target gene but separated by one two or more nucleotides in the sequence of the SSOMV. Such an SSOMV causes an insertion in the sequence of target gene.

The nucleotides of the SSOMV are deoxyribonucleotides that are linked by unmodified phosphodiester bonds except that the 3' terminal and/or 5' terminal internucleotide linkage or alternatively the two 3' terminal and/or 5' terminal internucleotide linkages can be a phosphorothioate or phosphoramidate. As used herein an internucleotide linkage is the linkage between nucleotides of the SSOMV and does not include the linkage between the 3' end nucleotide or 5' end nucleotide and a blocking substituent, see below.

The length of the SSOMV depends upon the type of cell in which the target gene is located. When the target gene is a chromosomal gene of an animal cell, e.g., a mammalian or avian cell, the SSOMV is between 25 and 65 nucleotides, preferably between 31 and 59 deoxynucleotides and most preferably between 34 and 48 deoxynucleotides. The total length of the homologous regions is usually the length of the SSOMV less one, two or three nucleotides. A mutator nucleotide can be introduce at more than one position in the SSOMV, which results in more than two homologous regions in the SSOMV. Whether there are two or more homologous regions, the lengths of at least two of the homologous regions should each be at least 8 deoxynucleotides.

For prokaryotic cells, the length of the is SSOMV is between 15 and 41 deoxynucleotides. The preferred length of the oligodeoxynucleotide for prokaryotic use depends upon the type of 3' protecting group that is used. When the 3' protecting substituent is a 3'-3' linked deoxycytidine, the oligonucleotide is preferably between about 21 and 28 deoxynucleotides, otherwise the optimal length is between 25 and 35 deoxynucleotides. The lengths of the homology regions are, accordingly, a total length of at least 14 deoxynucleotides and at least two homology regions should each have lengths of at least 7 deoxynucleotides.

For plant cells, the length of the SSOMV is between 21 and 55 deoxynucleotides and the lengths of the homology regions are, accordingly, a total length of at least 20 deoxynucleotides and at least two homology regions should each have lengths of at least 8 deoxynucleotides.

Within these ranges the optimal length of the oligodeoxynucletide is determined by the GC content, the higher the GC content the shorter the optimal oligodeoxynucleotide. However, a GC content greater than 50% is preferred.

The SSOMV can be used with any type of animal cell, e.g., a mamnalian cell, an avian cell, an insect cell, a fish cell, or a worm (nematode) cell. The SSOMV can also be used in any type of plant cell. Additionally, the SSOMV can be used with any type of bacterial cell, e.g., Gram-positive bacterial cells or Gram-negative bacterial cells. Exemplary types of bacteria include, *Salmonella, E. coli, Pseudomonas, Rostani*, etc. It is not important whether the cells are actively replicating or whether the target gene is transcriptionally active. However, when the target gene is located in a bacteria it is important that the bacteria be RecA⁺. Thus, most of the strains of bacteria commonly used in recombinant DNA work are not suitable for use in the present invention because such bacteria are RecA⁻ in order to reduce the genetic instability of the plasmids cloned therewith. Moreover, in bacterial cells the target gene can be located on a plasmid or on a bacterial artificial chromosome (BAC), as well as on the bacterial chromosome.

The SSOMV can be designed to be complementary to either the coding or the non-coding strand of the target gene. When the desired mutation is a substitution of a single base, it is preferred that the mutator nucleotide be a pyrimidine. To the extent that is consistent with achieving the desired functional result it is preferred that both the mutator nucleotide and the targeted nucleotide in the complementary strand be pyrimidines. Particularly preferred are SSOMV that encode transversion mutations, i.e., a C or T mutator nucleotide is mismatched, respectively, with a C or T nucleotide in the complementary strand.

In addition to the oligodeoxynucleotide the SSOMV can contain a 5' blocking substituent that is attached to the 5' terminal carbons through a linker. The chemistry of the linker is not critical other than its length, which should preferably be at least 6 atoms long and that the linker should be flexible.

The chemistry of the 5' blocking substituent for mammalian, avian or plant cells is not critical other than molecular weight which should be less than about 1000 daltons. A variety of non-toxic substituents such as biotin, cholesterol or other steroids or a non-intercalating cationic fluorescent dye can be used. For use in bacterial systems, however, the blocking substituent has a major effect on the efficiency of the SSOMV and it is preferably a 3,3,3',3'-tetramethyl N,N'-oxyalkyl substituted indocarbocyanine. Particularly preferred as reagents to make SSOMV are the reagents sold as Cy3™ and Cy5™ by Amersham Pharmacia Biotech, Piscataway, N.J., which are blocked phosphoroamidites that upon incorporation into an oligonucleotide yield 3,3,3',3'-tetramethyl N,N'-isopropyl substituted indomonocarbocyanine and indodicarbocyanine dyes, respectively. When the indocarbocyanine is N-oxyalkyl substituted it can be conveniently linked to the 5' terminal of the oligodeoxynucleotide through a phosphodiester with a 5' terminal phosphate. The chemistry of the dye linker between the dye and the oligodeoxynucleotide is not critical and is chosen for synthetic convenience. When the commercially available Cy3 phosphoramidite is used as directed the resulting 5' modification consists of a blocking substituent and linker together which are a N-hydroxypropyl, N'-phosphatidylpropyl 3,3,3',3'-tetramethyl indomonocarbocyanine.

In an alternative embodiment, the indocarbocyanine dye, e.g., Cy3 phosphoramidate, can be linked to the oligodeoxynucleotide after the oligodeoxynucleotide has been synthesized.

In the preferred embodiment the indocarbocyanine dye is tetra substituted at the 3 and 3' positions of the indole rings. Without limitation as to theory these substitutions prevent the dye from being an intercalating dye. The identity of the substituents at these positions are not critical.

The SSOMV can in addition have a 3' blocking substituent. Again the chemistry of the 3' blocking substituent is not critical, other than non-toxicity and molecular weight of less than about 1000, when the target gene is located in other than a bacterial cell. However, when the target gene is located in a bacterial cell the preferred 3' blocking substituent is a so-called inverted nucleotide, i.e., a nucleotide that is linked by an unsubstituted 3'-3' phosphodiester, as is taught by U.S. Pat. No. 5,750,669. In a more preferred embodiment the inverted nucleotide is a thymidine or most preferred a deoxycytidine. For use in bacterial cells, the combination of a Cy3 5' blocking substituent and an inverted deoxycytidine 3' blocking substituent is particularly preferred as the two modifications have a synergistic effect on the efficacy of the SSOMV. The SSOMV with the above recited modifications can be synthesized by conventional solid phase nucleotide synthesis.

The SSOMV can be introduced into the cell containing the target gene by the same techniques that are used to introduce the Kmiec type mutational vectors into animal and plant cells. For bacterial cells, a preferred method of introducing the SSOMV is by electroporation.

For use with animal cells, including mammalian and avian cells, the preferred method of delivery into the cell is by use of a protective macromolecular carrier. Commercially available liposomal transfecting reagents such LIPOFECTAMINE™ and SUPERFECT™ are designed so that the nucleic acid to be transfected is electrostatically adherent to the exposed surface of the liposome. Such carriers are not as preferred as protective macromolecular carriers. Suitable protective macromolecular carriers are disclosed in International Patent Publication WO 98/49350 and WO 99/40789 and in Bandyopadhyay et al., 1999, J. Biol. Chem. 274: 10163, which are each hereby incorporated by reference in their entirety.

A particularly preferred macromolecular carrier is an aqueous-cored lipid vesicle or liposome wherein the SSOMV is trapped in the aqueous core. Such vesicles are made by taking a solvent free lipid film and adding an aqueous solution of the SSOMV, followed by vortexing, extrusion or passage through a microfiltration membrane. In one preferred embodiment the lipid constituents are a mixture of dioleoyl phosphatidylcholine/dioleoyl phosphatidylserine/galactocerebroside at a ratio of 1:1:0.16. Other carriers include polycations, such as polyethylenimine, having a molecular weight of between 500 daltons and 1.3 Md, with 25 kd being a suitable species and lipid nanospheres, wherein the SSOMV is provided in the form of a lipophilic salt.

When the SSOMV are used to introduce genetic changes in mammalian and avian cells, it is preferred that the macromolecular carrier further comprise a ligand for a cell surface receptor that is internalized. Suitable receptors are the receptors that are internalized by the clathrin-coated pit pathway, such as the asialoglycoprotein receptor, the epidermal growth factor receptor and the transferin receptor. Also suitable are receptors that are internalized through the caveolar pathway such as the folic acid receptor. The galactocerebroside is a ligand for the asialoglycoprotein receptor. As used herein an internalizeable receptor is a receptor that is internalized by the clathrin-coated pit pathway or by the caveolar pathway.

The SSOMV can be used for any purpose for which the prior art mutational vectors were employed. Specific uses include the cure of genetic diseases by reversing the disease causing genetic lesion; such diseases includes for example hemophilia, $\alpha_1$ anti-trypsin deficiency and Crigler-Najjar disease and the other diseases that are taught by International Patent Publication WO 98/49350.

Alternatively, the SSOMV can be used to modify plants for the purposes described in patent publication WO 99/07865, which is hereby incorporated by reference in its entirety. An additional use of SSOMV in plants is the generation of herbicide resistant plants by means that avoid having to introduce a foreign or heterologous gene into a crop plant. Of particular interest is resistance to the herbicide glyphosate (ROUNDUP®). The identity of mutations that confer glyphosate resistance can be found in International Patent Publications WO 99/25853 and WO 97/04103.

Alternatively, the SSOMV can be used to modify bacteria. The use of SSOMV for the genetic manipulation of bacteria is particularly valuable in the fields of antibiotic production and in the construction of specifically attenuated bacteria for the production of vaccines. In both of the above applications it is important that antibiotic resistance genes not remain in the final modified bacteria.

Yet further, the SSOMV can be used in combination with a bacterial artificial chromosome (BAC) to modify a targeted gene from any species that has been cloned into a BAC. A fragment much larger than the targeted gene can be incorporated. The BAC having the cloned targeted gene is placed into a bacterial host and a predetermined genetic change is introduced according to the invention. A BAC subclone having the predetermined genetic change can be identified and the insert removed for further use. The present invention allows for the predetermined changes to be made without the time and expense attendant with obtaining making PCR fragments and inserting the fragments back into the original gene.

5. EXAMPLE 1

Treatment of the Gunn Rat

The Gunn rat contains a mutation in the UDP-glucuronosyltransferase gene, which is the same gene as is mutated in Crigler-Najjar Disease. Roy-Chowdhury et al., 1991, J. Biol. Chem. 266:18294; Iyanangi et al., 1989, J. Biol. Chem. 264:21302. In the Gunn rat there is a mutation at nucleotide 1206 that has deleted a G. A 35 nucleotide SSOMV, termed CN3-35UP, corresponding to the antisense strand, was constructed to reverse the mutation and has the following sequence: 5'-ATCATCGGCAGTCATTT C CAGGACAT-TCAGGGTCA-3' (SEQ ID NO: 1). CN3-35LOW, a second SSOMV that corresponds to the sense strand has the following sequence: 5'-TGACCCTGAATGTCCTG G AAAT-GACTGCCGATGAT-3' (SEQ ID NO: 2). The mutator nucleotide is in bold typeface.

5'Cy3, 3'-3' dC modified CN3-35UP (2 animals) and CN3-35LOW and unmodified CN3-35UP were formulated in an aqueous cored lipid vesicle having lipid constituents of dioleoyl phosphatidylcholine/dioleoyl phosphatidylserine/galactocerebroside at a ratio of 1:1:0.16. Approximately 2.0 ml of 5% dextrose containing 500 µg of the SSOMV was used to hydrate 2 mg of lipid, the vesicles were thereafter extruded to a diameter of 0.5 µm. Encapsulation efficiency was 80%. A positive control group was treated with Kmiec type MV (2 animals) given in an equimolar amount in the same carrier. Rats, weighing 250 grams, were treated on five consecutive days with 300 µg of SSOMV or the carrier. The resulting serum bilirubin levels were as follows in mg/dl.

| B/ days post | 0 d | 14 d | 21 d | 26 d | 39 d |
| --- | --- | --- | --- | --- | --- |
| Unmod-UP | 6.3 | 4.6 | 5.4 | 4.2 | 3.2 |
| Mod-UP | 7.9, 6.5 | 4.1, 3.3 | 4.9, 5.0 | 4.2, 3.8 | 3.6, 3.0 |
| Mod-LOW | 6.8 | 4.3 | 5.9 | 4.2 | 3.5 |
| Kmiec type | 6.3, 7.1 | 4.6, 5.7 | 4.8, 4.2 | 5.5, 5.1 | 4.4, 4.7 |

The data demonstrate that both modified and unmodified SSOMV and that both sense and antisense sequences were at least equivalent and at the longer time points SSOMV appeared superior to the Kmiec type mutational vectors.

6. EXAMPLE 2

Modification of the Human UDP-Glucuronosyltransferase Gene

The following example shows that an unmodified SSOMV in a macromolecular carrier can be used to introduce a specific genetic change in a mammalian cell in an artificial medium at rates that are within a factor of 3 of that seen with Kmiec type DNA/2'OMeRNA mutational vectors. The data further show that modifications as minimal as a single phosphorothioate linkage can result in fully comparable rates.

A group of Amish people have Crigler-Najjar Disease resulting from a C→A substitution at nucleotide 222 of the UDP-Glucuronosyltransferase gene. The mutation results in the conversion of a TAC (Tyr) to a TAA stop codon A SSOMV designed to introduce the disease causing mutation in a human hepatocellular carcinoma cell line, HuH-7 was designed. A 35 nucleotide SSOMV, designated CNAM3-35UP, or corresponds to the antisense strand and has the following sequence: 5'-GGGTACGTCTTCAAGGT T TAAAATGCTCCGTCTCT-3' (SEQ ID NO:3). The mutator nucleotide is in bold typeface.

HuH-7 cells at $10^6/cm^2$ were given 300 µl made in a carrier according to the method of Example 1 containing CNAM3-35UP, CNAM3-35UP, variously modified or an equimolar amount of an 82 nucleotide Kmiec type mutational vector. Cells were harvested and the relevant gene fragment was amplified by PCR, cloned and analyzed by allele specific hybridization according to the methods of Bandyopadhyay, supra. The following rates of conversion were observed:

| | |
| --- | --- |
| Unmodified SSOMV | 6% |
| 5'Cy3 SSOMV | 15% |
| 3'-3' dC SSOMV | 5% |
| 5'Cy3, 3'-3' dC SSOMV | 15% |
| 5'phos'thioate SSOMV | 16% |
| 3'phos'thioate | 12% |
| Kmiec type MV | 14%. |

These data demonstrate that in the presence of a macromolecular carrier, modified SSOMV were as effective as Kmiec type mutational vectors, and that unmodified SSOMV were as effective within a factor of 3.

7. EXAMPLE 3

Conversion of Kanamycin Resistance in a Bac

The following example shows that modified SSOMV are more effective than Kmiec DNA/2'OMeRNA mutational vectors in bacterial cells.

A kanamycin resistance gene was inactivated by the insertion of an inframe ATG stop codon. Kanamycin resistance is recovered by converting the third nucleotide to a C, i.e., making a transversion at the third nucleotide.

The sequence of a 41 nt SSOMV that corresponds to the sense strand for the recovery of Kanamycin resistance is as follows: 5'-GTGGAGAGGCTATTCGGCTA C GACTGGGCACAACAGACAAT-3' (SEQ ID NO: 4). The mutator nucleotide is in bold typeface.

To generate pBACKans, a BamHI linker was inserted into the unique SmaI site of pKans, and the resulting 1.3-kb BamHI-HindIII fragment containing the mutant kanamycin gene was inserted into the BamHI/HindIII sites of the BAC cloning vector pBeloBAC11 (Genome Systems, Inc., St. Louis, Mo.). *Escherichia coli* strains MC1061 and DH10B were transformed with pBACKans, selected on LB chloramphenicol plates, and made electrocompetent.

Forty μl of electrocompetent cells were electroporated with between 5 and 10 μg of SSOMV using the following conditions: 25 kV/cm, 200 ohms, 25 microfarads. 1 mL of SOC was added to cells immediately after electroporation and the culture grown for 1 hour while shaking at 37 C. 4 mL of LB+chloramphenicol (12.5 μg/mL final) was added and the cultures grown for an additional 2 hours while shaking at 37 C. Appropriate dilutions of the culture were plated on LB-chloramphenicol plates to assess viability and on LB-kanamycin plates to assess conversion. Conversion frequency was calculated by dividing the number of kanamycin resistant colonies/mL by the number of chloramphenicol resistant colonies/mL.

The rate of conversion observed with the 5'Cy3, 3'-3' dC modified 25 nucleotide SSOMV corresponded to about 1 conversion per 100 surviving bacteria. The relative rates of conversion were:

| | |
|---|---|
| 68 nt Kmiec MV w/2'OMe RNA linker | 0.04 |
| 68 nt Knijec MV w/DNA linker | 0.004 |
| 41 nt SSOMV w13',5' phos'thioate | 0.4 |
| 35 nt SSOMV w/3',5' phos'thioate | 4.0 |
| 29 nt SSOMV w/3t,5' phos'thioate | 0.9 |
| 25 nt SSOMV w/3t,5' phos'thioate | 1.0 |
| 41 nt SSOMV w/3'-3' dC,5'Cy3 | 2.0 |
| 35 nt SSOMV w/3t -3' dC,5'Cy3 | 2.9 |
| 35 nt SSOMV w/3'-3' dC, | 2.5 |
| 35 nt SSOMV w/5'Cy3 | 2.5 |
| 29 nt SSOMV w/3'-3' dC,5'Cy3 | 4.2 |
| 25 nt SSOMV w/3'-3' dC,5'Cy3 | 42.0 |
| 25 nt SSOMV w/3'-3' dC | 1.3 |
| 25 nt SSOMV w/5'Cy3 | 1.8 |
| 25 nt SSOMV w/3'phos'thioate,5'Cy3 | 8.4 |
| 35 nt SSOMV w/3'phos'thioate,5'Cy3 | 10.2 |

These data demonstrate that the rate of conversion of the optimal SSOMV was between $10^3$ and $10^4$ greater than that of the Kmiec type mutational vector.

8. EXAMPLE 4

The Use of an SSOMV Without a Protective Carrier in a Mammalian Cell-Hygromycin Resistance This example shows the modification of a mammalian cell using modified SSOMV in the absence of a protective macromolecular carrier. The modified SSOMV were able to introduce the genetic modification at a rate that was between 15 and 30 fold higher than the Kmiec type mutational vectors. This example uses the same gene as in Example 3; however, it is expressed in the HuH-7 cell line.

A clone of HuH7 cells containing a stably integrated copy of the mutant kanamycin gene in a IRES containing vector (pIRESKan-) were generated under hygromycin selection. Cells were cultured in DMEM high glucose/10% FBS containing 100 mg/ml hygromycin to maintain high expression from the integrated construct. Twenty four hours prior to transfection cells were seeded at a density of $1.0 \times 10^6$ cells in a 100 mm dish. Two hours prior to transfection the growth medium was replaced with 10 ml of OPTI-MEM™. Forty micrograms of oligonucleotide and 40 ml (80 μg) of LIPOFECTAMINE™ were diluted in separate tubes containing 200 ml of Opti-MEM pH 8.5. The LIPOFECTAMINE is then added to the oligonucleotide, mixed by pipette and incubated at room temperature for 30 minutes before the addition of 3.6 ml of Opti-MEM pH 8.5. The medium is aspirated from the cells and replaced with the 4 ml transfection mixture. The cells are incubated for 2 hours at 37° C. before the transfection mix is replaced with standard growth media. Two days post-transfection the cells are split into 2 100 mm dishes in 10 ml media containing 450 mg/ml G418. The G418 containing media is replaced daily for 10 days, then twice a week until colonies are macroscopically visible (16–18 days after transfection). Clones are picked approximately 21 days after transfection and expanded for molecular analysis.

Background rates of the development of hygromycin resistance is about 1 per $10^6$ When Kmiec type mutational vectors were employed there was no increase in the number of resistant colonies. Sequence analysis of one of 5 colonies showed that it had obtained the specific mutation. The mutations in the other 4 colonies could not be identified. When a 41 nucleotide SSOMV w/3'-3' dC,5'Cy3 was used, the rates of development of hygromycin resistant colonies increased by between 15 and 30 fold, i.e., to about 3 per $10^5$. Sequence analysis of these colonies showed that between 100% and 80% of the colonies had the correct genetic change. Experiments with 35 nt SSOMV w/3'-3' dC,5'Cy3 or w/3'phosphorthioate 5'Cy3 or w/two phosphorothioate linkages at each of the 3', 5' ends, each showed rates of development of hygromycin resistance that were about half that of the modified 41 nucleotide SSOMV.

9. EXAMPLE 5

The Use of an SSOMV Without a Protective Carrier in a Mammalian Cell-Tyrosinase This example shows that in a mammalian cell line an unmodified SSOMV without a protective carrier can be superior to both the 5' Cy3/3'-3' dC modified SSOMV and superior to Kmiec type DNA/2'OMe RNA mutational vectors.

These experiments use Melan-c, a murine melanocyte cell line having a C→G mutation at codon 82 of the tyrosinase gene, which creates an inframe stop. Bennett, et al., 1989, Development 105:379. A 35 nucleotide SSOMV which corresponds to the coding sequence was designed and has the following sequence: 5'-CCCCAAATCCAAACTTA C AGTTTCCGCAGTTGAAA-3' (SEQ ID NO: 5). The mutator nucleotide is in bold typeface.

Melan-c cells were cultured in RPMI medium containing 10% fetal bovine serum, 100 nM phorbol 12-myristate 13-acetate (PMA) and 0.1 mM b-mercaptoethanol (Gibco, Bethesda, Md.). Two days prior to transfection, cells were seeded at a density of $0.5-1.5 \times 10^5$ cells/well in a 6 six-well plate and refed with fresh medium 24 hours prior to transfection. Five to ten micrograms (220–440 nM) of the oligonucleotides, were incubated with 6–9 μg of Superfectin™ in 0.1 ml of TE (10 mM TRIS pH 7.5, 1 mM EDTA) for 30 min at room temperature. The transfection mixture was added to the cells containing 0.9 ml of DMEM high glucose growth media containing 10% serum and 100 nM PMA. After 6–18hours, cells were washed with phosphate-buffered saline and fed with 2 ml of the DMEM media. Cells were monitored for a change in pigmentation by microscopy.

The number of conversion events was determined by counting the number of pigmented cells or cell clusters 5 to 8 days after transfection.

The rates of albino→wild type (pigmented) conversion per $10^5$ cells as follows:

| | |
|---|---|
| Kmiec type MV | 1 |
| unmodified SSOMV | 5 |
| SSOMV w/3',5' phos'thioate | 6 |
| SSOMV w/3'-3'dC | 2 |
| SSOMV w/5'Cy3 | 3 |
| SSOMV w/3'-3'dC,5'Cy3 | 1 |

10. EXAMPLE 6

The Use of a Modified SSOMV in Plants

This example concerns the use of a SSOMV to introduce a Ser→Asn mutation at position 653 of the *Arabodopsis thaliana* acetohydroxyacid synthase (also known as acetolatate synthase). The mutation requires that an AGT codon be converted to a AAT codon and introduces resistance to imidazoline herbicides as well as sulfonyl urea herbicides. A 25 nucleotide SSOMV and a 35 nucleotide SSOMV were synthesized having 3'-3' dC and 5' Cy3 modifications and had the following sequences, respectively: 5'-CGATC-CCGA A TGGTGGCACTTT-3' (SEQ ID NO: 6), 5'-GT-TGCCGATCCCGA A TGGTGGCACTTTCAACG-3' (SEQ ID NO: 7). The mutator nucleotide is in bold typeface.

A disaggregated *A. thaliana* cell population was prepared plated at $10^6$ per plate and subjected to biolistic introduction of the SSOMV or a Kmiec type MV having the same sequence. Control plates using a plasmid determined that the efficiency of the biolistic system is about one delivery per 200 cells plated. After two months selection with 10 μM Imazaquin™ each of the biolistically treated cell populations showed a background corrected rate of Imazaquin resistance of about 1 per $10^3$ cells into which the mutational vectors had been successfully introduced.

11. EXAMPLE 7

Preparation of Folate-conjugated PEI

This example describes the preparation of folate-conjugated PEI which is suitable to use as a macromolecular carrier in the invention.

Folic acid (4.4 mg, 10 μmole) in sodium phosphate buffer (1.5 mL, 133 mM, pH 4.5) was treated with 200 μL pyridine and 1-(3-dimethylaminopropyl)-3-ethylcarbodiimide hydrochloride (EDC, 15.5. mg, 98 μmol) and incubated at room temperature for 1 hour. The activated folate solution (1.7 mL) was added to an aqueous solution of polyethyleneimine (25 kDa, 24.55 mg/mL; 1.02 mL) and incubated for 3 days at RT with gentle agitation. The conjugated polyethyleneimine was purified by dialysis against water through a 12 kDa MW cutoff membrane. The product was positive for amines by the ninhydrin assay and folate by UV absorbance with maxima at 259, 289 and 368 nm.

Coupling was about 1–2 folate moieties per 1000 amines which is equivalent to 1–2 folate per PEI molecule.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

We claim:

1. A method of obtaining an animal cell that contains a predetermined genetic change in a target gene which comprises:
   (a) providing a population of animal cells in a culture media;
   (b) adding to the culture media a composition comprising:
      (i) a single-stranded oligodeoxynucleotide having a 3' end nucleotide, a 5' end nucleotide, having at least 31 deoxynucleotides and not more than 59 deoxynucleotides, and having a sequence comprising at least two regions each of at least 8 deoxynucleotides that are each, respectively, identical to two regions of the targeted chromosomal gene, which regions together are at least 24 deoxynucleotides in length, and which regions are separated by at least one deoxynucleotide in the sequence of the targeted chromosomal gene or in the sequence of the oligodeoxynucleotide or both, such that the sequence of the oligodeoxynucleotide is not identical to the sequence of the targeted chromosomal gene; and
      (ii) a macromolecular carrier selected from the group consisting of:
         (A) an aqueous-cored lipid vesicle, wherein the aqueous core contains the single-stranded oligodeoxynucleotide, (B) a lipid nanosphere, which comprises a lipophilic salt of the single-stranded oligodeoxynucleotide, and (C) a polycation having an average molecular weight of between 500 daltons and 1.3 Md wherein the polycation forms a salt with the single-stranded oligodeoxynucleotide; and (c) identifying a cell of the population having the predetermined genetic change.

2. The method of claim 1, which further comprises isolating the identified cell.

3. The method of claim 1, in which the macromolecular carrier further comprises a ligand for an internalizeable receptor of the animal cell that is affixed to the surface of the macromolecular carrier.

4. The method of claim 3, in which the receptor is selected from the group consisting of an asialoglycoprotein receptor, a transferrin receptor and an epidermal growth factor receptor.

5. The method of claim 3, in which the receptor is the folic acid receptor.

6. The method of claim 1, in which the internucleotide linkage attached to the 3' end nucleotide is a phosphorothioate linkage.

7. The method of claim 1, in which the internucleotide linkage attached to the 5' end nucleotide is a phosphorothioate linkage.

8. The method of claim 1, in which the 5' hydroxyl of the 5' end nucleotide is attached to a 5' blocking substituent.

9. The method of claim 8, in which the 5' blocking substituent is a N'-hydroxyalkyl substituted 3,3,3',3'-tetra substituted indocarbocyanine dye, which is attached to the 5' hydroxyl through a linker.

10. The method of claim 9, in which the indocarbocyanine dye and linker together are a N-hydroxypropyl, N'-phosphatidylpropyl 3,3,3',3'-tetramethyl indomonocarbocyanine.

11. The method of claim 9, in which the internucleotide linkage attached to the 3' end nucleotide is a phosphorothioate linkage.

12. The method of claim 1, in which the 3' hydroxy of the 3' end nucleotide is attached to a 3' blocking substituent.

13. The method of claim 12, in which the 3' blocking substituent is a blocking nucleotide that is 3'-3' linked to the 3' hydroxy of the 3' end nucleotide.

14. A method of obtaining an animal cell that contains a predetermined genetic change in a target gene which comprises:

(a) providing a population of animal cells in a culture media;

(b) adding to the culture media a compound comprising a single-stranded oligodeoxynucleotide having a 3' end nucleotide, a 5' end nucleotide, having at least 25 deoxynucleotides and not more than 65 deoxynucleotides and having a sequence comprising at least two regions each of at least 8 deoxynucleotides that are each, respectively, identical to at least two regions of the targeted chromosomal gene, which regions together are at least 24 deoxynucleotides in length, and which regions are separated by at least one deoxynucleotide in the sequence of the targeted chromosomal gene or in the sequence of the oligodeoxynucleotide or both, such that the sequence of the oligodeoxynucleotide is not identical to the sequence of the targeted chromosomal gene; and (c) identifying a cell of the population having the predetermined genetic change.

15. The method of claim 14, in which the internucleotide linkage attached to the 3' end nucleotide is a phosphorothioate linkage.

16. The method of claim 15, in which the internucleotide linkage attached to the 5' end nucleotide is a phosphorothioate linkage.

17. A method of obtaining an animal cell that contains a predetermined genetic change in a target gene which comprises:

(a) providing a population of animal cells in a culture media;

(b) adding to the culture media a compound comprising a single-stranded oligodeoxynucleotide having a 3' end nucleotide, a 5' end nucleotide, having at least 25 deoxynucleotides and not more than 65 deoxynucleotides and having a sequence comprising at least two regions each of at least 8 deoxynucleotides that are each, respectively, identical to at least two regions of the targeted chromosomal gene, which regions together are at least 24 deoxynucleotides in length, and which regions are separated by at least one deoxynucleotide in the sequence of the targeted chromosomal gene or in the sequence of the oligodeoxynucleotide or both, such that the sequence of the oligodeoxynucleotide is not identical to the sequence of the targeted chromosomal gene, and which internucleotide linkage attached to both the 5' end nucleotide and 3' end nucleotide is a phosphorothioate linkage; and (c) identifying a cell of the population having the predetermined genetic change.

18. The method of claim 15, in which an N'-hydroxyalkyl substituted 3,3,3',3'-tetra substituted indocarbocyanine dye is attached to the 5' hydroxyl of the 5' end nucleotide through a linker.

19. The method of claim 14, in which the internucleotide linkage attached to the 5' end nucleotide is a phosphorothioate linkage.

20. The method of claim 19, in which the internucleotide linkage attached to the 3' end nucleotide is a phosphorothioate linkage or in which a deoxycytidine or thymidine nucleotide is 3'-3' linked to the 3' hydroxy of the 3' end nucleotide or both.

21. The method of claim 1 in which the animal cell is selected from the group consisting of a mammalian cell, an avian cell, an insect cell, a worm cell and a fish cell.

22. The method of claim 14 or 17 in which the animal cell is selected from the group consisting of a mammalian cell, an avian cell, an insect cell, a worm cell and a fish cell.

* * * * *

SEQUENCE LISTING

```
<160> NUMBER OF SEQ ID NOS: 7

<210> SEQ ID NO 1
<211> LENGTH: 35
<212> TYPE: DNA
<213> ORGANISM: Artificial Sequence
<220> FEATURE:
<223> OTHER INFORMATION: single-stranded oligodeoxynucleotide mutational
      vector

<400> SEQUENCE: 1
atcatcggca gtcatttcca ggacattcag ggtca                                   35

<210> SEQ ID NO 2
<211> LENGTH: 35
<212> TYPE: DNA
<213> ORGANISM: Artificial Sequence
<220> FEATURE:
<223> OTHER INFORMATION: single-stranded oligodeoxynucleotide mutational
      vector

<400> SEQUENCE: 2
tgaccctgaa tgtcctggaa atgactgccg atgat                                   35

<210> SEQ ID NO 3
<211> LENGTH: 35
```

-continued

```
<212> TYPE: DNA
<213> ORGANISM: Artificial Sequence
<220> FEATURE:
<223> OTHER INFORMATION: single-stranded oligodeoxynucleotide mutational
      vector

<400> SEQUENCE: 3
gggtacgtct tcaaggttta aaatgctccg tctct                               35

<210> SEQ ID NO 4
<211> LENGTH: 41
<212> TYPE: DNA
<213> ORGANISM: Artificial Sequence
<220> FEATURE:
<223> OTHER INFORMATION: single-stranded oligodeoxynucleotide mutational
      vector

<400> SEQUENCE: 4
gtggagaggc tattcggcta cgactgggca caacagacaa t                        41

<210> SEQ ID NO 5
<211> LENGTH: 35
<212> TYPE: DNA
<213> ORGANISM: Artificial Sequence
<220> FEATURE:
<223> OTHER INFORMATION: single-stranded oligodeoxynucleotide mutational
      vector

<400> SEQUENCE: 5
ccccaaatcc aaacttacag tttccgcagt tgaaa                               35

<210> SEQ ID NO 6
<211> LENGTH: 22
<212> TYPE: DNA
<213> ORGANISM: Artificial Sequence
<220> FEATURE:
<223> OTHER INFORMATION: single-stranded oligodeoxynucleotide mutational
      vector

<400> SEQUENCE: 6
cgatcccgaa tggtggcact tt                                             22

<210> SEQ ID NO 7
<211> LENGTH: 32
<212> TYPE: DNA
<213> ORGANISM: Artificial Sequence
<220> FEATURE:
<223> OTHER INFORMATION: single-stranded oligodeoxynucleotide mutational
      vector

<400> SEQUENCE: 7
gttgccgatc ccgaatggtg gcactttcaa cg                                  32
```